(12) United States Patent
Rosekrans et al.

(10) Patent No.: US 9,072,851 B2
(45) Date of Patent: Jul. 7, 2015

(54) TRACHEAL TUBE WITH FACILITY TO VIEW INNER CANNULA

(75) Inventors: Brian Rosekrans, Lyons, CO (US); Seamus Maguire, Athlone (IE); Roger Harrington, Athlone (IE)

(73) Assignee: COVIDIEN LP, Mansfield, MA (US)

( * ) Notice: Subject to any disclaimer, the term of this patent is extended or adjusted under 35 U.S.C. 154(b) by 262 days.

(21) Appl. No.: 13/307,330

(22) Filed: Nov. 30, 2011

(65) Prior Publication Data

US 2013/0133644 A1    May 30, 2013

(51) Int. Cl.
*A61M 16/04*    (2006.01)
*A61M 16/08*    (2006.01)

(52) U.S. Cl.
CPC ....... *A61M 16/0465* (2013.01); *A61M 16/0434* (2013.01); *A61M 16/0497* (2013.01); *A61M 16/0816* (2013.01); *A61M 2205/057* (2013.01); *A61M 2205/583* (2013.01); *A61M 2205/584* (2013.01); *A61M 2209/06* (2013.01); *A61M 16/0427* (2014.02)

(58) Field of Classification Search
CPC ............ A61M 16/04; A61M 16/0465; A61M 16/0488; A61M 16/0497; A61M 16/0402; A61M 16/0816; A61M 16/0434; A61M 16/0427
USPC ........ 128/207.14–207.18; 604/19, 21, 23, 26, 604/27, 43, 48, 506, 510, 514, 516, 93.01, 604/103.01, 156–163, 164.01–170.03, 264, 604/529; 600/117; 606/108
See application file for complete search history.

(56) References Cited

U.S. PATENT DOCUMENTS

| | | | | |
|---|---|---|---|---|
| 3,890,976 | A | * | 6/1975 | Bazell et al. ............. 128/207.15 |
| 4,033,353 | A | * | 7/1977 | La Rosa .................... 128/207.15 |
| 4,072,054 | A | * | 2/1978 | Blouin et al. .................. 374/151 |
| 4,909,248 | A | | 3/1990 | Anderson et al. |
| 4,981,470 | A | * | 1/1991 | Bombeck, IV ............... 600/350 |
| 5,259,371 | A | * | 11/1993 | Tonrey ...................... 128/200.26 |
| 5,309,902 | A | * | 5/1994 | Kee et al. .................. 128/202.27 |
| 5,489,275 | A | * | 2/1996 | Thompson et al. ........... 604/264 |
| 5,623,924 | A | * | 4/1997 | Lindenman et al. ..... 128/207.17 |
| 6,102,041 | A | | 8/2000 | Boussignac et al. |
| 6,378,522 | B1 | * | 4/2002 | Pagan ...................... 128/207.14 |
| 6,722,369 | B1 | | 4/2004 | Kron |
| 6,994,088 | B2 | | 2/2006 | Briggs, III |

(Continued)

FOREIGN PATENT DOCUMENTS

| | | |
|---|---|---|
| EP | 2086619 A1 | 8/2009 |
| WO | 2008045418 A1 | 4/2008 |

OTHER PUBLICATIONS

Silicone Cuffless and Silicone Air Cuff Tracheostomy Tubes, Arcadia Medical Products Brochure; 2010.

(Continued)

*Primary Examiner* — Valerie L Skorupa
(74) *Attorney, Agent, or Firm* — Fletcher Yoder PC

(57) ABSTRACT

A tracheal tube assembly includes an outer cannula configured to be positioned in a patient airway and an inner cannula configured to be disposed inside the outer cannula. The tracheal tube assembly further includes a flange member secured about the outer cannula, and a connector coupled to a proximal end of the outer cannula. The connector is configured to provide a view of the inner cannula, and the inner cannula and the connector form a contiguous passageway for exchanging fluid with the patient airway in operation.

20 Claims, 5 Drawing Sheets

(56) References Cited

U.S. PATENT DOCUMENTS

| | | |
|---|---|---|
| 7,086,402 B2 | 8/2006 | Peterson |
| 7,305,989 B2 * | 12/2007 | Gostelow ................. 128/207.14 |
| 7,448,387 B2 | 11/2008 | Janatpour |
| 2003/0196659 A1 | 10/2003 | Gradon et al. |
| 2005/0161047 A1 | 7/2005 | Briggs, III |
| 2007/0083262 A1 | 4/2007 | Matlock |
| 2007/0255258 A1 | 11/2007 | Matlock et al. |
| 2008/0216839 A1 | 9/2008 | Rutter |
| 2011/0259338 A1 * | 10/2011 | Worley ................... 128/207.14 |

OTHER PUBLICATIONS

Rusch Disposable Inner Cannulas, Teleflex Medical Products Brochure; 2010.

Percutan Sets for Percutaneous Tracheostomy; Tracoe Medical GmbH Products Brochure; 2010.

Tracoe Twist; Tracoe Medical GmbH Products Brochure; 2010.

* cited by examiner

TRACHEAL TUBE WITH FACILITY TO VIEW INNER CANNULA

BACKGROUND

The present disclosure relates generally to the field of tracheal tubes and, more particularly, to a tracheal tube having viewable inner cannulas.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of situations exist in which artificial ventilation of a patient may be desired. For short-term ventilation or during certain surgical procedures, endotracheal tubes may be inserted through the mouth to provide oxygen and other gasses to a patient. For other applications, particularly when longer-term intubation is anticipated, tracheostomy tubes may be preferred. Tracheostomy tubes are typically inserted through an incision made in the neck of the patient and through the trachea. A resulting stoma is formed between the tracheal rings below the vocal chords. The tracheostomy tube is then inserted through the opening. In general, two procedures are common for insertion of tracheostomy tubes, including a surgical procedure and a percutaneous technique.

Such tubes may include an inner cannula, such as a reusable inner cannula, or a disposable inner cannula. The inner cannula may be disposed inside the tracheostomy tube and used as a conduit for liquids or gas incoming and outgoing into the patient's lungs. The inner cannula may be removed for cleaning and for disposal of secretions without disturbing the placement of the tracheostomy tube. A connector is typically provided at an upper or proximal end where the tube exits the patient airway, suitable for coupling the ventilator with the inner cannula. In one embodiment, the inner cannula may be removed, cleaned, and reused. In another embodiment, the inner cannula may be disposable, and a new inner cannula may then be positioned inside of the tracheal tube. By enabling the cleaning and/or replacement of the inner cannula, a ventilation circuit may be kept clean and free of secretions.

Standard connectors have been developed to allow the tracheal tube to then be fluidly coupled to artificial ventilation equipment to supply the desired air or gas mixture to the patient, and to evacuate gases from the lungs. One difficulty that arises in the use of tracheal tubes, and tracheostomy tubes in particular, is in the connection of the tube to the ventilation equipment. For example, an inner cannula may not be installed, or may be installed improperly. This may lead to difficulties with ventilation when a connection is made to ventilation equipment.

There is a need, therefore, for improved tracheal tubes, and particularly for improved tracheostomy tubes. It would be desirable to provide a tube that allows for greater facility in visually observing the proper placement of the inner cannula during ventilation and enabling the changing of the inner cannula while facilitating the proper positioning of the inner cannula.

BRIEF DESCRIPTION

This disclosure provides a novel tracheal tube designed to respond to such needs. The tube allows for the visual inspection of an inner cannula before, during, and after ventilation activities. Indeed, a clinician may visually observe the placement of the inner cannula of the tube even while the patient is undergoing ventilation activities. In a tracheostomy tube embodiment, for example, a flange member fits adjacent to the neck of a patient and an end connector is provided, extending proximally from the flange member and outwardly from the neck. The tracheostomy tube includes an inner cannula, such as a colored inner cannula. In one embodiment, the end connect further includes one or more windows suitable for viewing the inner cannula. The windows may include markings denoting a desired position of the inner cannula within the tracheostomy tube. In another embodiment, the end connector may be transparent, translucent, or more generally, of a composition that enables the viewing of the inner cannula through the entirety of the end connector. In yet another embodiment, the end connector may include a transparent or translucent portion, suitable for observing the placement of the inner cannula. Additionally, the tracheal tube may be magnetic resonance imaging (MRI) compatible, thus allowing for artificial ventilation during MRI procedures.

Thus, in accordance with a first aspect, a tracheal tube assembly includes an outer cannula configured to be positioned in a patient airway and an inner cannula configured to be disposed inside the outer cannula. The tracheal tube assembly further includes a flange member secured about the outer cannula, and a connector coupled to a proximal end of the outer cannula. The connector is configured to provide a view of the inner cannula, and the inner cannula and the connector form a contiguous passageway for exchanging ventilator gases, atmospheric gases, or fluid with the patient airway in operation.

In accordance with another aspect, a tracheal tube assembly kit comprises an outer cannula configured to be positioned in a patient airway and a flange member configured to be secured about the cannula. The tracheal tube assembly kit further includes a first inner cannula comprising a first color and configured to be positioned inside the outer cannula. The tracheal tube assembly kit also includes a window disposed on the outer cannula and having a translucency suitable for viewing an inner cannula. The tracheal tube assembly kit additionally includes an end connector coupled to a proximal end of the outer cannula. The proximal protrusion is configured to couple with the second connector of the extension tube and the distal protrusion is configured to couple with the cannula or flange member.

Also disclosed herein is a tracheal tube assembly comprising an outer cannula configured to be positioned in a patient airway and a window having a translucency suitable for viewing an inner cannula. The tracheal tube assembly further includes a flange member secured about the outer cannula, and an end connector coupled to a proximal end of the outer cannula. The window is disposed in at least one of the outer cannula or the end connector.

BRIEF DESCRIPTION OF THE DRAWINGS

Various aspects of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
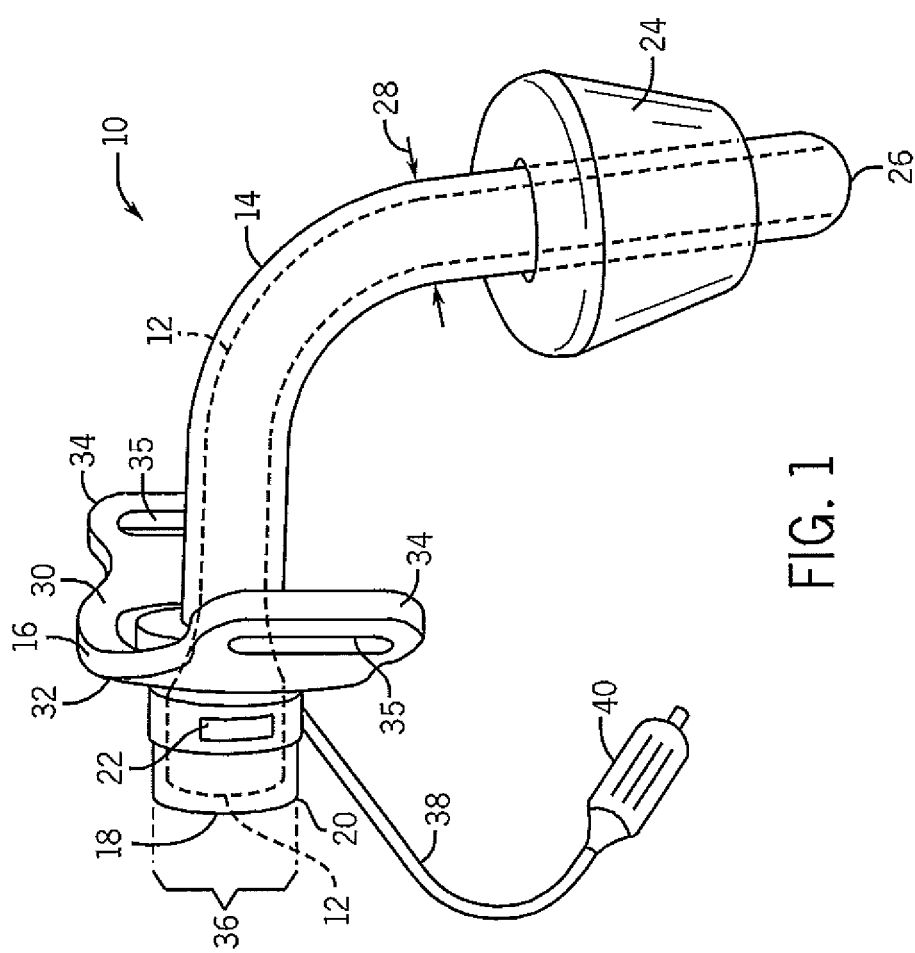
FIG. 1 is a perspective view of an exemplary tracheal tube in accordance with aspects of the present techniques.

A tracheal tube according to a preferred embodiment is illustrated in FIG. 1. The tracheal tube assembly 10 represented in the figures is a tracheostomy tube, although aspects of this disclosure could be applied to other tracheal tube structures, such as endotracheal tubes. The application to a tracheostomy tube is apt, however, insomuch as such tubes tend to be worn for longer periods of time, and thus may include a removable and/or disposable inner cannula 12 shown disposed inside of an outer cannula 14, useful in maintaining a clean ventilation circuit.

The outer cannula 14 is illustrated extending both distally as well as proximally from a flange member 16. The inner cannula 12 may be provided in different colors, and may be introduced through an opening 18 of an end connector 20 inside of the outer cannula 14. In the depicted embodiment, a window 22 is provided, suitable for viewing the colored inner cannula 12 through the end connector 20. In use, the window 22 enables the visual inspection of the colored inner cannula 12, thus insuring a proper placement of the inner cannula 12 and minimizing or eliminating situations where the user or clinician may forget to introduce the inner cannula 12.

During intubation, the tracheal tube assembly 10 is placed through an opening formed in the neck and trachea of a patient, and extending into the patient airway. The embodiment illustrated in the figures includes a sealing cuff 24, although in practice a wide range of tube designs may be used, including tubes having no cuffs or tubes having multiple cuffs around the outer cannula 14. The inner cannula 12 in the illustrated embodiment forms a conduit from which liquids or gases, including medications, may enter through the proximal opening 18 an exit through a distal opening 26. The cannula has an outer dimension 28 allowing it to fit easily through an incision made in the neck and trachea of the patient. In practice, a range of such tubes may be provided to accommodate the different contours and sizes of patients and patient airways. Such tube families may include tubes designed for neonatal and pediatric patients as well as for adults. By way of example only, outer dimension 28 of the outer cannula 14 may range from 4 mm to 16 mm.

In one embodiment, the outer cannula 14 enters the flange member 16 along a lower face 30 and protrudes through an upper face 32 of the flange member 16. When in use, the face 30 will generally be positioned against the neck of a patient, with the cannula extending through an opening formed in the neck and trachea. A pair of side wings or flanges 34 extend laterally and serve to allow a strap or retaining member (not shown) to hold the tube assembly in place on the patient. In the illustrated embodiment, apertures 35 are formed in each side flange 34 to allow the passage of such a retaining device. In many applications, the flange member 16 may be taped or sutured in place as well.

The end connector 20 is formed in accordance with industry standards to permit and facilitate connection to ventilating equipment (not shown). By way of example, standard outer dimensions may be provided as indicated at reference numeral 36 that allow a mating connector piece to be secured on the connector shown. By way of example, a presently contemplated standard dimension 36 accommodates a 15 mm connector, although other sizes and connector styles may be used. In use, then, air or other gas may be supplied through the connector and the inner cannula 12, and gases may be extracted from the patient. For example, the tube assembly 10 may be inserted into the patient's airway, and the cuff 24 may then be inflated through an inflation lumen 38. A pilot balloon 40 may then indicate that air is in the cuff 24, thus sealing the patient's airway. Once the tracheal tube is positioned and secured, a ventilator may be coupled to the end connector 20, as described in more detail below with respect to FIG. 2. By providing for the window 22 and other viewing embodiments described herein, the tube assembly 10 may enable a more efficient ventilation circuit and prevent errors, such as ventilating the tube assembly 10 that is missing the inner cannula 12.

Figure 2:
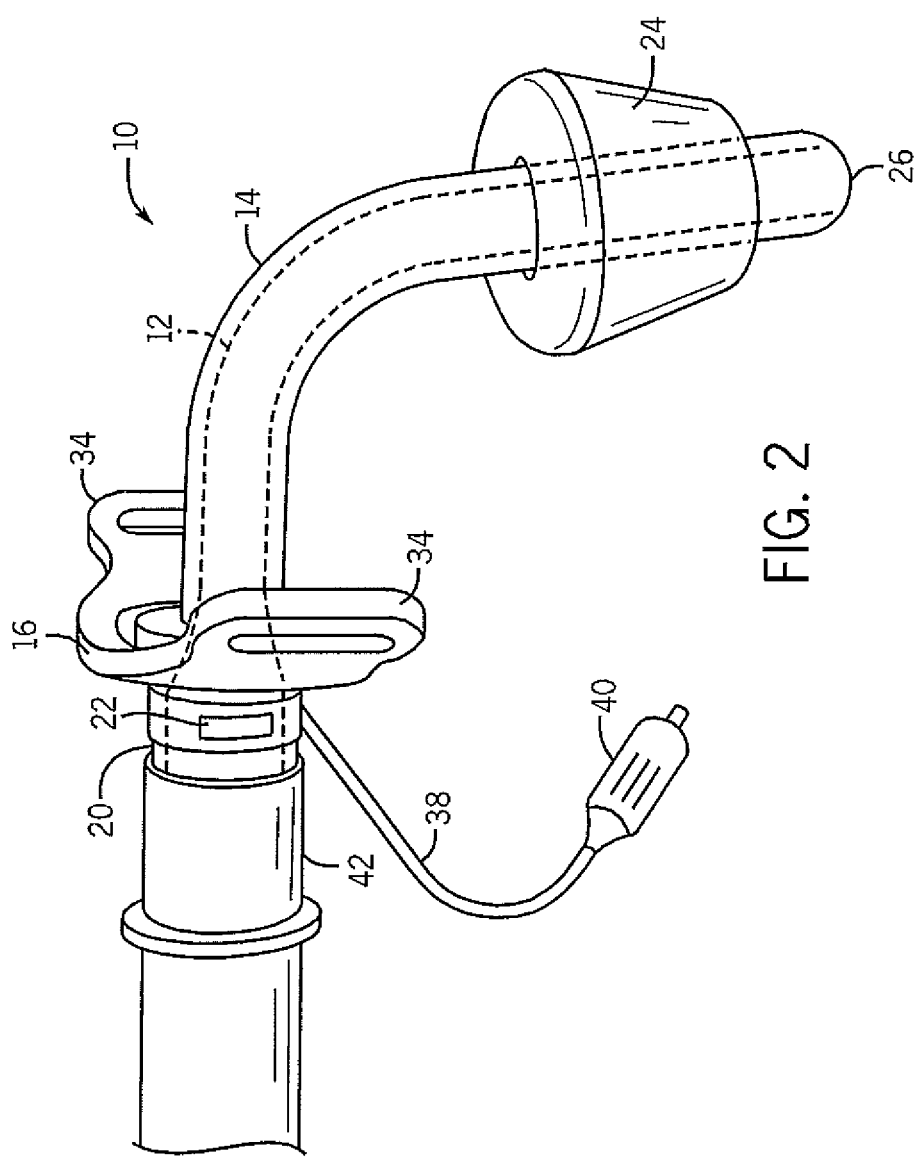
FIG. 2 is a perspective view of the exemplary tracheal tube of FIG. 1 fluidly coupled to a ventilation tube.

FIG. 2 illustrates the tracheal tube assembly 10 fluidly coupled to a ventilation tube 42. Because the figure includes like elements found in FIG. 1, these elements are denoted using like reference numbers. As mentioned above, the tracheal tube assembly 10 may be connected to a ventilator (not shown) attached to the ventilation tube 42 and used to enable an assisted airway circuit through the patient's lungs. Additionally, the tracheal tube assembly 10 may be connected to other medical devices, such as a suction device, a T-junction, a medicine delivery system, and so forth. Indeed, the end connector 20 may enable the attachment of one or more medical devices to the tracheal tube assembly 10. Accordingly, the window 22 may be used to verify the presence and proper placement of the colored inner cannula 12, thus providing for visual confirmation that the tube assembly 10 has been properly assembled.

In the illustrated embodiment, the window 22 is a rectangular piece that is disposed within the end connector 20, as described in more detail below with respect to FIG. 3. In other embodiments, the window 22 may be provided in other shapes, such as a circle, a square, a triangle, a parallelogram, a hexagon, and so on. Additionally, more than one window 22 may be used. For example, a second window may be provided on a side of the end connector directly opposite the illustrated window 22. Accordingly, the presence and the positioning of the inner cannula 12 may be easily detected through a visual inspection, even during ventilation operations. For example, the window 22 may be used to insert and verify the position of the inner cannula 12, as described in more detail below with respect to FIG. 3.

Figure 3:
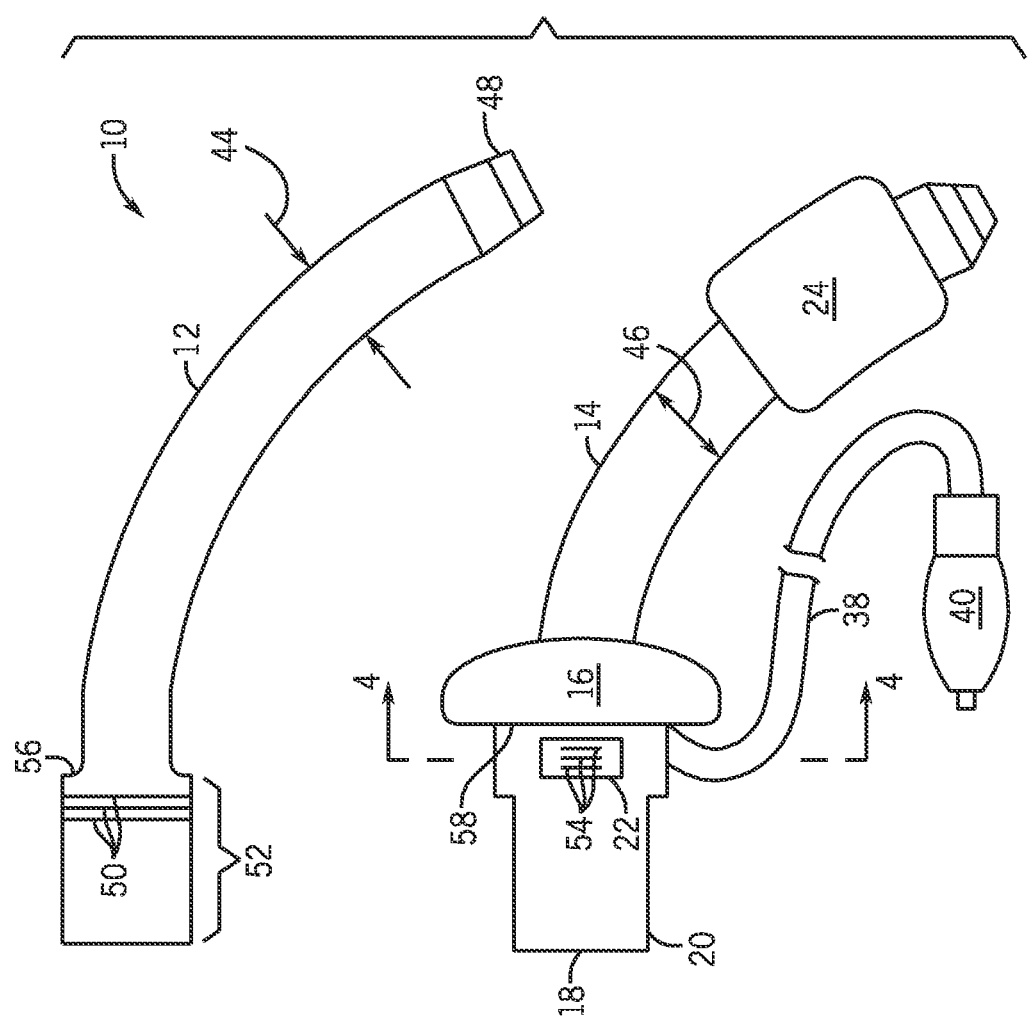
FIG. 3 is a side view of certain functional parts of the tube shown in FIG. 1 prior to in situ assembly.

FIG. 3 is a side view illustrating the inner cannula 12 and the remainder of the tube assembly 10 components (e.g., outer cannula 14, flange member 16, end connector 20, window 22, cuff 24, lumen 38, and pilot balloon 40) prior to in situ assembly of the inner cannula 12 into the outer cannula 14. Indeed, illustrated components may be provided as a tube assembly kit, and the user or clinician may perform final assembly of the tracheal tube 10 by selecting a desired inner cannula 12 and then inserting the inner cannula 12 into the outer cannula 14, prior to intubation. Thus assembled, the tracheal tube 10 may then be inserted into the patient's trachea.

The inner cannula 12 may be selected to include certain properties, such as a preferred color and an outer diameter. In one embodiment, the colors may be provided in solid colors, such as red, orange, yellow, green, blue, indigo, violet, and so on. In other embodiments, the colors may be provided in patterns, such as stripped patterns, dotted patterns, mixed with solid colors, or a combination thereof. The outer diameter 44 may be selected to approximate an inner diameter 46 of the outer cannula 14, but outer diameters 44 smaller than the inner diameter 46 may also be selected. For example, a kit may include multiple inner cannulas 12, each having different colors and outer diameters 44.

A distal end 48 of the inner cannula 12 may then be manually inserted inwardly into the outer cannula 14 through the opening 18. During insertion the window 22 may be used to observe the inner cannula 12. In one embodiment, markings 50 disposed on a proximal portion 52 of the inner cannula 12 may be used as a reference for a desired insertion point. In one example, the inner cannula 12 may be inserted into the outer cannula 14 until the markings 50 are disposed approximately in the center of the window 22. In another example, the inner cannula 12 may be inserted into the outer cannula 14 until the markings 50 are disposed correlative with markings 54 of the window 22. In yet another example, no markings may be provided, and the inner cannula 12 may be inserted so that a rear wall 56 of the proximal portion 52 abuts against a rear wall 58 of the end connector 20. By providing for markings 50, 54 and/or abutment walls 56, 58, the inner cannula 12 may be properly positioned. During ventilation activities, the clinician may easily verify the presence of the inner cannula 12, as well as the position of the inner cannula 12 relative to the outer cannula 14. In this manner, inadvertent errors, such as improperly positioning the inner cannula 12, or forgetting to insert the inner cannula 12, may be prevented.

Different techniques may be used to manufacture the tube assembly 10. The end connector 20 may be molded, overmolded, computer numerical control (CNC) machined, milled, or otherwise formed into the desired shape. In one embodiment, a mold or machine used to manufacture the end connector 20 may produce the end connector 20 having a slot sized to fit the window 22. The window 22 may then be added to the end connector 20, for example, by overmolding, gluing, thermally bonding, or more generally, attaching the window 22 to the end connector 20. In another embodiment, a multi-shot injection mold process, such as a "two shot" process, may be used. In the first shot, the slotted end connector 20 may be molded, followed by a second shot molding the window 22, or vice versa.

The end connector 20 may be manufactured of materials such as a polyvinyl chloride (PVC), a PEBAX silicone, a polyurethane, thermoplastic elastomers, a polycarbonate plastic, a silicon, or an acrylonitrile butadiene styrene (ABS). Likewise, the window 22 may be manufactured out of clear or translucent material, including PVC, PEBAX silicone, polyurethane, thermoplastic elastomers, polycarbonate plastic, silicon, or ABS. It is to be noted, that the window 22 may be manufactured in different levels of translucency. That is, the windows 22 may be completely transparent, or include various degrees of translucency suitable for allowing observation of the inner cannula 12 and/or the markings 50 through the window 22. Accordingly, the inner cannula 12 may be properly positioned, the tracheal tube assembly 10 inserted into the patient's trachea, and the cuff 24 sealingly inflated through the balloon 40 and inflation lumen 38. The tube assembly 10 may then be connected to the ventilation tube 42 shown in FIG. 2, and the patient ventilated as desired. It is to be noted, that in another, example, the window 22 is not provided. Instead, the end connector 20 is provided in a clear or translucent material, including PVC, PEBAX silicone, polyurethane, thermoplastic elastomers, polycarbonate plastic, silicon, or ABS having a translucency suitable for viewing the inner cannula 12 through the end connector 20. In yet another example, the window 22 may be disposed on any location on the outer cannula 14.

Figure 4:
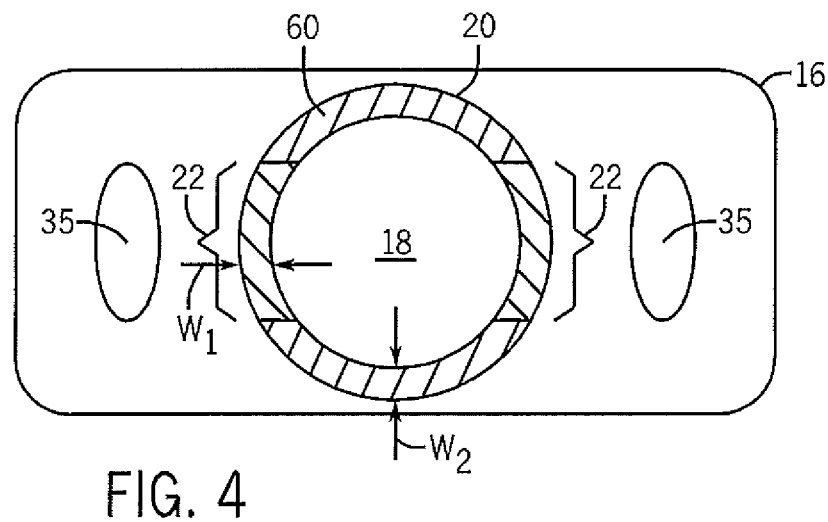
FIG. 4 is a sectional view of certain functional parts of the tube shown in FIG. 3, taken through line 4 of FIG. 3.

FIG. 4 illustrates a cross sectional view taken through line 4-4 of FIG. 3. In the illustration, two windows 22 are provided. Indeed, the end connector 20 may include multiple windows 22, thus providing for viewing positions circumferentially disposed around the end connector 20. For example, 3, 4, 5 or 6 windows 22 may be provided. Accordingly, the user or clinician may verify the positioning of the inner cannula 12 through a variety of different locations and angles. The figure further illustrates the width of the window 22. As depicted, the window 22 is manufactured as including a width $w_1$ equal to a width $w_2$ of walls 60 of the end connector 20. Accordingly, indentions or protrusions in the interior opening 18 caused by the windows 22 are minimized or eliminated, enabling a smooth flow of fluid through the opening 18.

Figure 5:
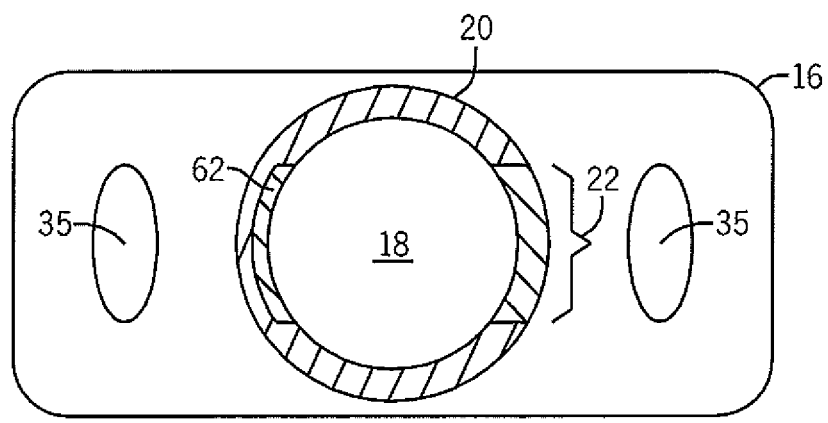
FIG. 5 is a sectional view of other embodiments of certain functional parts of the tube shown in FIG. 3, taken through line 4 of FIG. 3.

In one embodiment, markings 62 disposed internally to the end connector and directly opposite to the window 22 may be used, as illustrated in FIG. 5. The markings 62 may be provided in a different color than the color used for the inner cannula 12. Accordingly, the markings 62 may be used in verifying the proper insertion of the inner cannula 12. In one example, as the inner cannula 12 is inserted into the outer cannula 14, the inner cannula 12 occludes or otherwise covers the markings 62. The inner cannula 12 may be properly inserted when the markings 62 are completely occluded. In one manufacturing embodiment, the markings 62 may be placed by inserting a brush through the opening 18 and painting the markings 62 inside of the end connector 20. In another embodiment, the markings 62 may be printed, for example, by using a laser printer, an inkjet printer, a thermal printer, a transfer/pad printer (e.g., applying an image to a surface), and so on. In yet another embodiment, the markings 62 may be machined, milled, molded or overmolded in the end connector 20. The markings may also be placed using the "double shot" process mentioned above, with a first shot used to injection mold the end connector 20 and the second shot used to injection mold the markings 62, or vice versa. Likewise, the markings 54 of the window 22 and/or window 64 (described below with respect to FIG. 6) may be brushed, printed, machined, milled, molded or overmolded.

Figure 6:
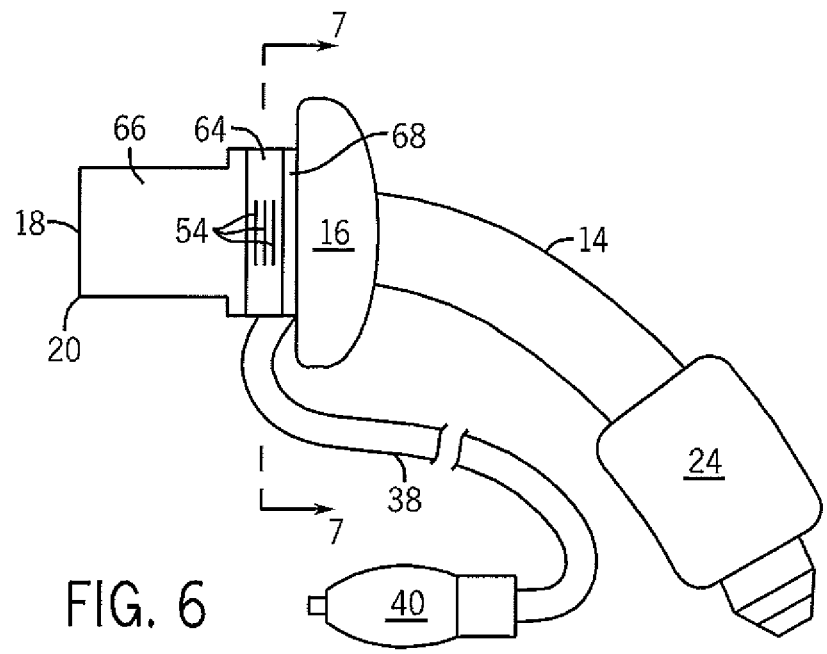
FIG. 6 is a side view of the a tracheal tube having an annular window.

FIG. 6 is a side view illustrating the use of an annular window 64. In the illustrated embodiment, the annular window 64 is disposed circumferentially on the end connector 20, thus providing for a number of viewing positions at various locations around the end connector 20. By increasing the viewing area around the end connector 20, the annular window 64 improves visibility and may enable a more efficient positioning of the inner cannula 12 inside of the outer cannula 14. In one embodiment, the end connector 20 may be manufactured as three components, a proximal component 66, the annular window 64, and a distal component 68. The three components may then be bonded, glued, molded, overmolded, or otherwise adhered to each other. For example, the multi-shot molding process described above may be used to mold the components 66 and 68 out of an opaque material (e.g., PVC, PEBAX silicone, polyurethane, thermoplastic elastomers, polycarbonate plastic, silicon, or ABS) and the window 64 out of a translucent material (e.g., translucent PVC, PEBAX silicone, polyurethane, thermoplastic elastomers, polycarbonate plastic, silicon, or ABS).

The annular window 64 may also include the markings 54 suitable for aiding the positioning of the inner cannula 12 into the outer cannula 14. For example, the inner cannula 12 may be inserted into the outer cannula 14 until the markings 50 of the inner cannula 12 are disposed correlative with the markings 54 of the window 64. In this manner, the inner cannula 12 may be placed at the desired position inside of the cannula 14. In one embodiment, the annular window 64 may be provided as a ring or toroid with an arc having 360° of circumference (defining a circle). In another embodiment, the annular window 64 may be provided as a partial ring with an arc having less than 360° of circumference, as described in more detail below with respect to FIG. 7.

Figure 7:
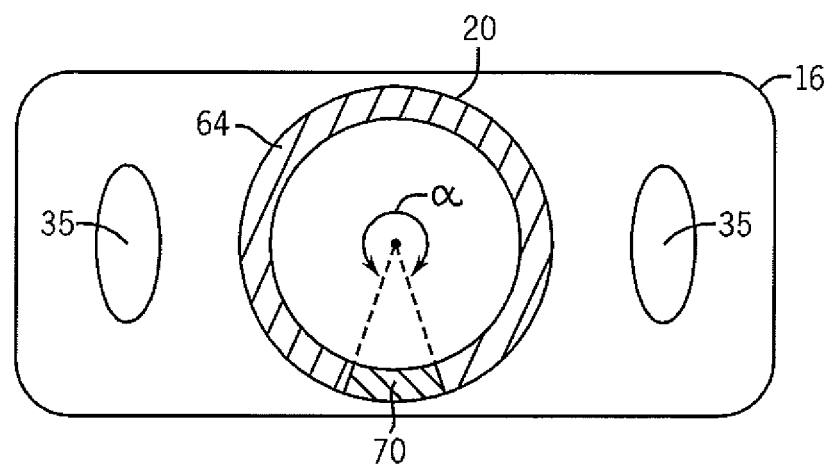
FIG. 7 is a sectional view of certain functional parts of the tube shown in FIG. 6, taken through line 7 of FIG. 6.

FIG. 7 is a sectional view taken through line 7-7 of FIG. 6, depicting the annular window 64 positioned on the end connector 20. In the depicted embodiment, the annular window 64 includes an arc having an angle α of less than 360°. By providing for the annular window 64 as a partial ring having an arc with angle α of less than 360°, certain regions of the end connector 20, e.g., portion 70, may also be used as an attachment region for assembling the annular window 64 as a component of the end connector 20. In one embodiment, the portion 70 may be included in the component 66 shown in FIG. 6. In another embodiment, the portion 70 may be included in the component 68 shown in FIG. 6. Accordingly, the coupling between the components 64, 66, and 68 may be improved. Likewise, because of the higher cost of the translucent material used in manufacturing the annular window 64 when compared to the cost of non-translucent material, the end connector 20 embodiment depicted in FIG. 7 may be manufactured at a reduced cost when compared to embodiments having a full ring annular window 64.

What is claimed is:

1. A tracheal tube assembly comprising:
    an outer cannula configured to be positioned in a patient airway;
    an inner cannula configured to be disposed inside the outer cannula;
    a flange member secured about the outer cannula; and
    a connector disposed on a proximal end of the outer cannula and comprising a window having a translucency suitable to view the inner cannula through the window, wherein the connector is configured to couple the outer cannula to a ventilator and to provide a view of the inner cannula, wherein an inner cannula rear wall corresponding to an inner cannula proximal portion abuts against a connector rear wall when the inner cannula is disposed inside the outer cannula, and wherein the inner cannula and the connector form a contiguous passageway with the ventilator for exchanging fluid with the patient airway in operation.

2. The tracheal tube assembly of claim 1, wherein the connector comprises a second window having the translucency suitable to view the inner cannula through the second window.

3. The tracheal assembly of claim 2, wherein the second window is disposed opposite the window.

4. The tracheal tube assembly of claim 1, wherein the window comprises an arc of 360° or less.

5. The tracheal tube assembly of claim 1, wherein the window comprises a window width equal to a width of the connector.

6. The tracheal tube assembly of claim 1, wherein the connector a is formed from a material having the translucency suitable to view the inner cannula through the connector.

7. The tracheal tube assembly of claim 1, wherein the inner cannula comprises a marking configured to visually mark a desired position of the inner cannula inside of the outer cannula.

8. The tracheal tube assembly of claim 7, wherein the marking of the inner cannula is disposed correlative to a connector marking.

9. The tracheal tube assembly of claim 8, wherein the inner cannula covers the connector marking when disposed in the outer cannula to visually mark a desired position of the inner cannula inside the outer cannula.

10. The tracheal tube assembly of claim 1, wherein the connector comprises a marking configured to visually mark a desired position of the inner cannula inside of the outer cannula.

11. The tracheal tube assembly of claim 1, wherein the window comprises a marking configured to visually mark a desired position of the inner cannula inside of the outer cannula.

12. The tracheal tube assembly of claim 1, comprising a protrusion on a connector proximal end, wherein the protrusion enables coupling of the outer cannula to the ventilator, and wherein the protrusion surrounds at least a portion of an inner cannula proximal end.

13. A tracheal tube assembly kit comprising:
    an outer cannula configured to be positioned in a patient airway;
    a flange member configured to be secured about a proximal end of the outer cannula, wherein the flange member is adapted to abut the patient neck when the outer cannula is inserted into the patient airway;
    a first inner cannula comprising a first color and configured to be positioned inside the outer cannula, wherein an inner cannula proximal end is within a proximal end of the outer cannula;
    an end connector coupled to the proximal end of the outer cannula, wherein a proximal protrusion is configured to couple with a second connector of an extension tube and a distal protrusion is configured to couple with the outer cannula or the flange member; and
    a window disposed on the end connector proximal of the flange member and configured to permit viewing the first inner cannula when inserted, wherein the window is distal to the proximal end of the outer cannula and an inner cannula proximal end.

14. The assembly kit of claim 13, comprising a second inner cannula having a second color different from the first color.

15. The assembly kit of claim 14, wherein the first inner cannula comprises a first outer diameter (OD) different from a second OD included in the second inner cannula.

16. The assembly kit of claim 13, wherein the window comprises a marking configured to visually mark a desired position of the inner cannula inside of the outer cannula.

17. A tracheal tube assembly comprising:
    an outer cannula configured to be positioned in a patient airway;
    a window having a translucency suitable to view an inner cannula disposed inside the outer cannula;

a flange member secured about a proximal end of the outer cannula and configured to abut the patient's neck when the outer cannula is inserted into the patient's airway; and an end connector coupled to a proximal end of the outer cannula, wherein the window is disposed proximal of the flange member in the end connector and is distal to the proximal end of the outer cannula.

18. The tracheal tube assembly of claim 17, wherein the inner cannula comprises a marking configured to visually mark a desired position of the inner cannula inside of the outer cannula.

19. The tracheal tube assembly of claim 17, wherein the connector comprises an internal connector marking, wherein the inner cannula covers the connector markings to visually mark a desired position of the inner cannula inside the outer cannula.

20. The tracheal tube assembly of claim 17, wherein the window is adjacent to a distal end of the end connector.

* * * * *